US012629464B2

(12) United States Patent
Smith et al.

(10) Patent No.: US 12,629,464 B2
(45) Date of Patent: May 19, 2026

(54) DEVICES FOR DELIVERING AT LEAST ONE FLOWING MEDIA, ASSOCIATED SENSOR MODULES, AND ASSOCIATED METHODS OF MECHANICALLY AND ELECTRICALLY COUPLING A SENSOR MODULE TO A DEVICE FOR DELIVERING AT LEAST ONE FLOWING MEDIA

(71) Applicant: Honeywell International Inc.,
Charlotte, NC (US)

(72) Inventors: Jessica Nicole Smith, Dublin, OH
(US); Richard Andrew Wade,
Worthington, OH (US)

(73) Assignee: Honeywell International Inc.,
Charlotte, NC (US)

( * ) Notice: Subject to any disclaimer, the term of this
patent is extended or adjusted under 35
U.S.C. 154(b) by 381 days.

(21) Appl. No.: 18/201,955

(22) Filed: May 25, 2023

(65) Prior Publication Data

US 2024/0390568 A1     Nov. 28, 2024

(51) Int. Cl.
*A61M 1/36*       (2006.01)
*A61M 1/16*       (2006.01)
*H05K 5/06*       (2006.01)
(52) U.S. Cl.
CPC ........ *A61M 1/3639* (2013.01); *A61M 1/1601*
(2014.02); *H05K 5/061* (2013.01); *A61M*
*2205/3334* (2013.01)
(58) Field of Classification Search
CPC .............. A61M 1/3639; A61M 1/1601; A61M
2205/3334; A61M 1/3663; A61M 1/367;
(Continued)

(56) References Cited

U.S. PATENT DOCUMENTS 4,672,997 A * 6/1987 Landis ................. G01F 1/6847
73/202.5
4,829,818 A * 5/1989 Bohrer ................. G01F 1/6845
73/204.22
(Continued)

FOREIGN PATENT DOCUMENTS

EP            1026985 B1    1/2006
JP       2010-538745 A    12/2010
(Continued)

OTHER PUBLICATIONS

Sensirion, "Single-Use Liquid Flow Sensor," 2 pages, (May 19,
2022). [Retrieved from the Internet Nov. 6, 2023: URL: <https://
sensirion.com/media/documents/D3A97DA0/6165A23D/Sensirion_
Liquid_Flow_Meters_Flyer_LD20-Series.pdf>].
(Continued)

*Primary Examiner* — David J Bolduc
(74) *Attorney, Agent, or Firm* — Alston & Bird LLP

(57) ABSTRACT
A device for delivering a flowing media is provided. For
example, a device for delivering a flowing media may
include a housing defining an opening, a first printed circuit
board assembly (PCBA), a fluid-resistant seal occluding the
opening, and a sensor module. The sensor module comprises
a second PCBA having a plurality of electrical contact pads;
a sensing element in electrical communication with one or
more of the electrical contact pads; and a flow tube at least
partially defining a flow path for conveying a flowing media
therethrough. The flow tube comprises an elongated main
body disposed proximate the first major surface of the
second PCBA such that the flow path is disposed proximate
the sensing element such that at least a portion of the flowing
media makes direct contact with the sensing element. The
sensor module is selectively mechanically and electrically
attachable to the device.

19 Claims, 11 Drawing Sheets

(58) Field of Classification Search
CPC ....... H05K 5/061; G01F 15/18; A61B 5/6866;
G01D 21/02
See application file for complete search history.

(56) References Cited

U.S. PATENT DOCUMENTS

| | | | |
|---|---|---|---|
| 4,920,972 A | 5/1990 | Frank et al. | |
| 5,081,866 A * | 1/1992 | Ochiai | G01F 15/00 |
| | | | 600/537 |
| 5,228,329 A * | 7/1993 | Dennison | G01H 3/005 |
| | | | 73/49.1 |
| 5,750,892 A * | 5/1998 | Huang | G01F 15/00 |
| | | | 73/202 |
| 5,752,918 A | 5/1998 | Fowler et al. | |
| 6,117,086 A | 9/2000 | Shulze | |
| 6,311,561 B1 | 11/2001 | Bang et al. | |
| 6,619,142 B1 | 9/2003 | Forster et al. | |
| 6,655,207 B1 * | 12/2003 | Speldrich | G01F 1/40 |
| | | | 73/202.5 |
| 2003/0195452 A1 * | 10/2003 | Hunley | A61M 1/3609 |
| | | | 604/4.01 |
| 2006/0137444 A1 * | 6/2006 | Kuzuyama | G01F 5/00 |
| | | | 73/202 |
| 2009/0249869 A1 | 10/2009 | Meier et al. | |
| 2010/0286599 A1 | 11/2010 | Ziegler et al. | |
| 2011/0186177 A1 * | 8/2011 | Lanier, Jr. | A61M 5/14248 |
| | | | 141/383 |
| 2013/0008263 A1 * | 1/2013 | Kabasawa | G01F 1/6845 |
| | | | 73/861 |
| 2014/0046260 A1 * | 2/2014 | Kamen | A61B 5/150175 |
| | | | 604/890.1 |
| 2014/0054883 A1 * | 2/2014 | Lanigan | A61M 39/12 |
| | | | 285/33 |
| 2015/0157537 A1 * | 6/2015 | Lanigan | G01F 11/086 |
| | | | 141/349 |
| 2015/0367053 A1 | 12/2015 | Bellei et al. | |
| 2017/0059374 A1 * | 3/2017 | DeKalb | A61M 5/172 |
| 2018/0085551 A1 * | 3/2018 | Krietzman | H05B 1/0252 |
| 2020/0164132 A1 * | 5/2020 | Loderer | A61B 5/14542 |
| 2022/0161021 A1 * | 5/2022 | Mitze | A61M 60/839 |
| 2023/0014838 A1 * | 1/2023 | Miller | A61M 16/049 |
| 2023/0389229 A1 * | 11/2023 | Buchert | H05K 5/061 |
| 2024/0009371 A1 * | 1/2024 | Patrinicola | A61M 3/0279 |

FOREIGN PATENT DOCUMENTS

| | | |
|---|---|---|
| JP | 2018-531397 A | 10/2018 |
| JP | 2018-531654 A | 11/2018 |
| JP | 2018-535416 A | 11/2018 |
| JP | 2019-527083 A | 9/2019 |
| JP | 2021-500162 A | 1/2021 |
| JP | 2022-527215 A | 5/2022 |
| WO | 2009/035773 A1 | 3/2009 |
| WO | 2019/083939 A1 | 5/2019 |
| WO | 2020/210221 A1 | 10/2020 |

OTHER PUBLICATIONS

ShinEtsu, "Inter-Connectors," 2 pages, (Dec. 3, 2022). [Retrieved from the Internet Nov. 6, 2023: URL: <https://www.shinpoly.com/products/inter-connectors/>].
English Translation of JP Office Action dated Feb. 4, 2025 for JP Application No. 2024075180, 3 page(s).
JP Office Action Mailed on Feb. 4, 2025 for JP Application No. 2024075180, 2 page(s).
Extended European Search Report Mailed on Oct. 9, 2024 for EP Application No. 24170455, 8 page(s).
English Translation of JP Office Action dated Sep. 1, 2025 for JP Application No. 2024075180, 4 page(s).
JP Office Action Mailed on Sep. 1, 2025 for JP Application No. 2024075180, 4 page(s).
English Translation of JP Office Action dated Mar. 30, 2026 for JP Application No. 2024075180, 4 page(s).
JP Office Action Mailed on Mar. 30, 2026 for JP Application No. 2024075180, 4 page(s).

* cited by examiner

40

46B

46A

48A

42

48A

44

DEVICES FOR DELIVERING AT LEAST ONE FLOWING MEDIA, ASSOCIATED SENSOR MODULES, AND ASSOCIATED METHODS OF MECHANICALLY AND ELECTRICALLY COUPLING A SENSOR MODULE TO A DEVICE FOR DELIVERING AT LEAST ONE FLOWING MEDIA

FIELD OF THE INVENTION

Embodiments of the present disclosure generally relate to devices for delivering at least one flowing media, and, more particularly, to such devices having selectively attachable sensor modules.

BACKGROUND

There are many different devices for delivering a flowing media. Some of these devices use one or more sensor modules to measure one or more characteristics of the flowing media. For example, the one or more sensor modules may measure the flow rate or the pressure of the flowing media.

Some of these devices are used in the medical field. For example, a hemodialysis device pumps blood from a patient to a filter that removes waste from the blood, typically via a dialysate, and then pumps the blood back to the patient. Such hemodialysis devices often have one or more pressure sensor modules that measure the pressure of the blood as it is being pumped to the filter and as it is being pumped back to the patient.

Applicant has identified many technical challenges and difficulties associated with such devices for delivering a flowing media and associated sensor modules. Through applied effort, ingenuity, and innovation, many of these identified problems have been solved by developing solutions that are included in embodiments of the present disclosure, many examples of which are described in detail herein.

BRIEF SUMMARY

Various embodiments described herein relate to devices for delivering at least one flowing media, associated sensor modules, and associated methods of mechanically and electrically coupling a sensor module to a device for delivering at least one flowing media.

In accordance with various embodiments of the present disclosure, a device for delivering at least one flowing media is provided. In some embodiments, the device for delivering at least one flowing media comprises a housing defining an opening, a first printed circuit board assembly (PCBA) disposed within the housing, a fluid-resistant seal occluding the opening, and a sensor module. The sensor module comprises (i) a second printed circuit board assembly (PCBA) having a first major surface and an opposing second major surface having a plurality of electrical contact pads, (ii) a sensing element disposed on the first major surface of the second PCBA and in electrical communication with one or more of the plurality of electrical contact pads, and (iii) a flow tube at least partially defining a flow path for conveying a flowing media therethrough. The flow tube comprises an elongated main body disposed proximate the first major surface of the second PCBA such that the flow path is disposed proximate the sensing element such that at least a portion of the flowing media makes direct or indirect contact with the sensing element. The sensor module is selectively attachable to the device such that the second PCBA is aligned with the fluid-resistant seal when the sensor module is selectively attached to the device. One or more of the plurality of electrical contact pads are adapted to complete an electrical connection between the sensing element and the device via physical contact with at least a portion of the device.

In some embodiments, a plurality of spring-loaded electrical connector pins are disposed in the fluid-resistant seal such that a first end of each of the plurality of spring-loaded electrical connector pins is positioned outside of the housing and a second end of each of the plurality of spring-loaded electrical connector pins is electrically connected to the first PCBA. The electrical connection between the sensing element and the device is completed via contact by each of the plurality of electrical contact pads with the first end of a corresponding one of the plurality of spring-loaded electrical connector pins.

In some embodiments, one or more of the plurality of electrical contact pads are arcuate.

In some embodiments, the plurality of electrical contact pads is a first plurality of electrical contact pads, the first PCBA comprises a second plurality of electrical contact pads, the fluid-resistant seal comprises a compression-type electrically conductive membrane, and the electrical connection between the sensing element and the device is completed via contact by each of the first plurality of electrical contact pads with the compression-type electrically conductive seal and contact by each of the second plurality of electrical contact pads with the compression-type electrically conductive seal.

In some embodiments, the sensor module is selectively attachable to the device via a twist-lock mechanism.

In some embodiments, the device further comprises a grasping handle selectively attachable to the sensor module to enable a user to rotate the sensor module to engage the twist-lock mechanism.

In some embodiments, the flow tube is affixed to the second PCBA via a first connector and a second connector, the first and second connectors being affixed to the second PCBA on opposing sides of the sensing element.

In some embodiments, the sensing element is a first sensing element, the flow tube is a first flow tube, the flow path is a first flow path, the flowing media is a first flowing media, and the sensor module further comprises a second sensing element disposed on the first major surface of the second PCBA and in electrical communication with one or more of the plurality of electrical contact pads and a second flow tube at least partially defining a second flow path for conveying a second flowing media therethrough. The second flow tube comprises an elongated main body disposed substantially parallel to the first flow tube and proximate the first major surface of the second PCBA such that the second flow path is disposed proximate the second sensing element such that at least a portion of the second flowing media makes direct or indirect contact with the second sensing element.

In accordance with various embodiments of the present disclosure, a sensor module comprises a printed circuit board assembly (PCBA) having a first major surface and an opposing second major surface, the second major surface having a plurality of electrical contact pads, a sensing element disposed on the first major surface of the PCBA and in electrical communication with one or more of the plurality of electrical contact pads, and a flow tube at least partially defining flow path for conveying a flowing media therethrough. The flow tube comprises an elongated main body disposed proximate the first major surface of the PCBA such that the flow path is disposed proximate the sensing element such that at least a portion of the flowing media makes direct or indirect contact with the sensing element. One or more of the plurality of electrical contact pads are adapted to complete an electrical connection between the sensing element and a device to which the sensor module is selectively attached via physical contact with at least a portion of the device.

In accordance with various embodiments of the present disclosure, a method for mechanically and electrically coupling a sensor module to a device for delivering at least one flowing media comprises providing a device for delivering at least one flowing media and providing a sensor module. The device for delivering at least one flowing media comprises (i) a housing defining an opening, (ii) a first printed circuit board assembly (PCBA) disposed within the housing, (iii) a fluid-resistant seal occluding the opening, and (iv) first and second twist-lock arms proximate opposing edges of the fluid-resistant seal. The sensor module comprises (i) a second printed circuit board assembly (PCBA) having a first major surface and an opposing second major surface, the second major surface having a plurality of electrical contact pads, (ii) a sensing element disposed on the first major surface of the second PCBA and in electrical communication with one or more of the plurality of electrical contact pads, and (iii) a flow tube at least partially defining a flow path for conveying a flowing media therethrough. The flow tube comprises an elongated main body disposed proximate the first major surface of the second PCBA such that the flow path is disposed proximate the sensing element such that at least a portion of the flowing media makes direct or indirect contact with the sensing element. The method further comprises positioning the sensor module such that the second PCBA is aligned with the fluid-resistant seal and the flow tube is insertable between the first and second twist-lock arms, pushing the sensor module against the device, and rotating the sensor module such that at least a first portion of the flow tube is captured by the first twist-lock arm and at least a second portion of the flow tube is captured by the second twist-lock arm. One or more of the plurality of electrical contact pads complete an electrical connection between the sensing element and the device via physical contact with at least a portion of the device.

The foregoing illustrative summary, as well as other exemplary objectives and/or advantages of the disclosure, and the manner in which the same are accomplished, are further explained in the following detailed description and its accompanying drawings.

BRIEF DESCRIPTION OF THE DRAWINGS

The description of the illustrative embodiments may be read in conjunction with the accompanying figures. It will be appreciated that, for simplicity and clarity of illustration, elements illustrated in the figures have not necessarily been drawn to scale, unless described otherwise. For example, the dimensions of some of the elements may be exaggerated relative to other elements, unless described otherwise. Embodiments incorporating teachings of the present disclosure are shown and described with respect to the figures presented herein, in which.

DETAILED DESCRIPTION OF THE INVENTION

Figure 1:
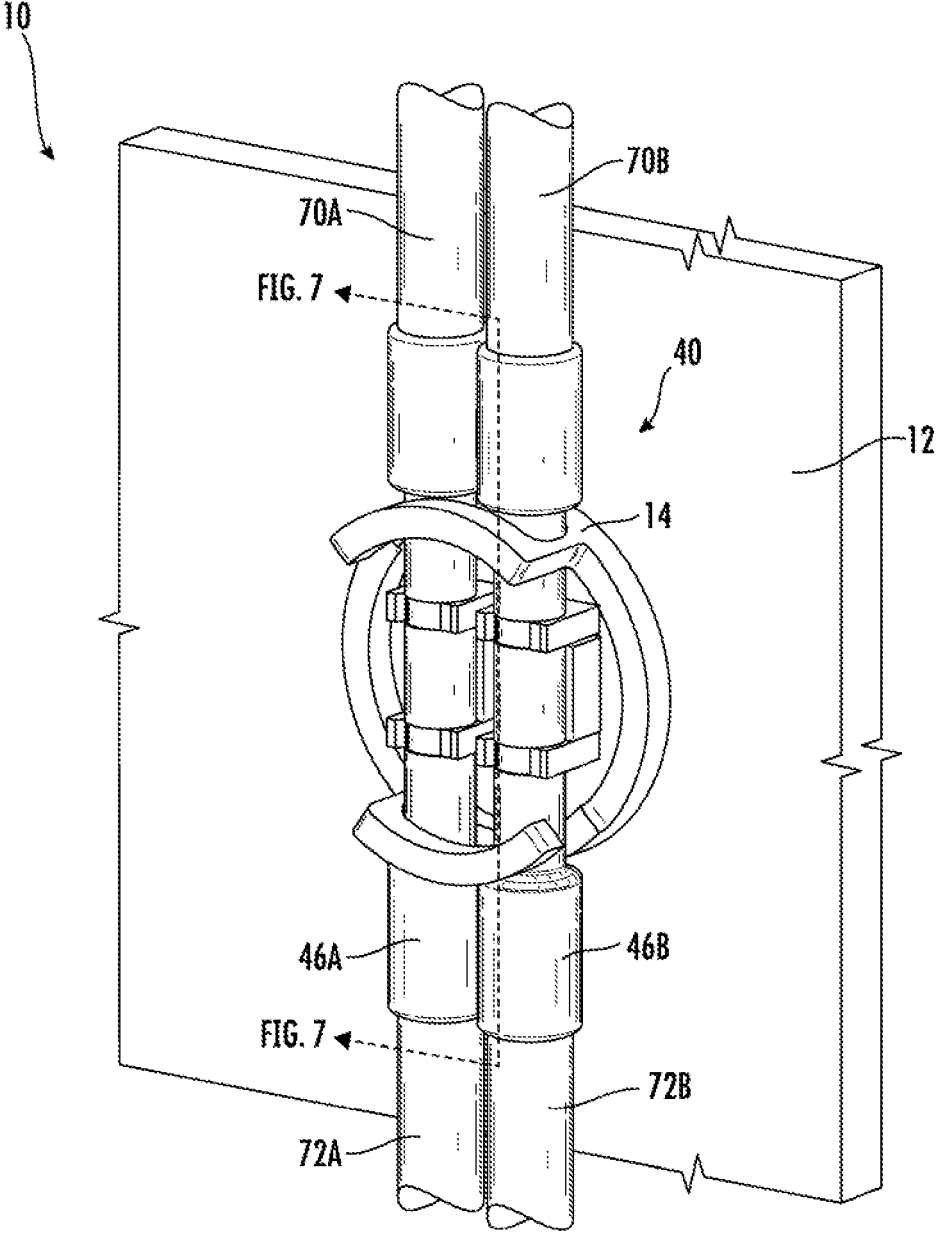
FIG. 1 is a front perspective view of an example device for delivering at least one flowing media, with an attached sensor module, in accordance with some embodiments of the present disclosure.

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout.

As used herein, terms such as "front," "rear," "top," "bottom," "left," "right," etc. are used for explanatory purposes in the examples provided below to describe the relative position of certain components or portions of components. Furthermore, as would be evident to one of ordinary skill in the art in light of the present disclosure, the terms "substantially" and "approximately" indicate that the referenced element or associated description is accurate to within applicable engineering tolerances.

As used herein, the term "comprising" means including but not limited to and should be interpreted in the manner it is typically used in the patent context. Use of broader terms such as comprises, includes, and having should be understood to provide support for narrower terms such as consisting of, consisting essentially of, and comprised substantially of.

The phrases "in one embodiment," "according to one embodiment," "in some embodiments," and the like generally mean that the particular feature, structure, or characteristic following the phrase may be included in at least one embodiment of the present disclosure and may be included in more than one embodiment of the present disclosure (importantly, such phrases do not necessarily refer to the same embodiment).

The phrases "in one example," "according to one example," "in some examples," and the like generally mean that the particular feature, structure, or characteristic following the phrase may be included in at least one example of the present disclosure and may be included in more than one example of the present disclosure (importantly, such phrases do not necessarily refer to the same example).

If the specification states a component or feature "may," "can," "could," "should," "would," "preferably," "possibly," "typically," "optionally," "for example," "as an example," "in some examples," "often," or "might" (or other such language) be included or have a characteristic, that specific component or feature is not required to be included or to have the characteristic. Such component or feature may be optionally included in some examples, or it may be excluded.

The word "example" or "exemplary" is used herein to mean "serving as an example, instance, or illustration." Any implementation described herein as "example" or "exemplary" is not necessarily to be construed as preferred or advantageous over other implementations.

The term "electrically coupled," "electrically coupling," "electrically couple," "electrically connected," "electrically connecting," "electrically connect," "in communication with," or "in electronic communication with" in the present disclosure refers to two or more elements or components being connected through wired means and/or wireless means, such that signals, electrical voltage/current, data and/or information may be transmitted to and/or received from these elements or components.

The term "in fluid communication with" in the present disclosure refers to two or more elements or components being connected through one or more paths or pathways, such that a fluid or other flowing media may be input to and/or output from these elements or components.

The term "component" may refer to an article, a device, or an apparatus that may comprise one or more surfaces, portions, layers and/or elements. For example, an example component may comprise one or more substrates that may provide underlying layer(s) for the component and may comprise one or more elements that may form part of and/or are disposed on top of the substrate. In the present disclosure, the term "element" may refer to an article, a device, or an apparatus that may provide one or more functionalities.

The term "sensor module" refers to a component that may detect, measure, and/or identify any one or more attributes or characteristics of a flowing medium or media, including but not limited to flow rate(s) and/or pressure(s). In the present disclosure, the term "flowing medium" or "flowing media" refers to a substance or substances (such as, but not limited to, liquid substance and/or gaseous substance) that can move or progress freely through a flow path of a sensor module. In the present disclosure, the term "fluid" refers to a substance (such as, but not limited to, liquid substance and/or gaseous substance) that is capable of flowing.

The term "flow path" refers to a passageway through which a flowing media may flow, traverse, or be conveyed. An example flow path of the present disclosure may be defined/formed by and/or comprise one or more channels.

The term "device for delivering at least one flowing media" refers to any device capable of conveying, such as via one or more pumps and one or more lengths of tubing, a flowing media as defined above from a first location to a second location.

As described above, devices for delivering at least one flowing media are often used in the medical field. For example, such devices may be used for hemodialysis, in which the device pumps blood from a patient to a filter that removes waste from the blood and then pumps the blood back to the patient. Similar applications include therapeutic plasma exchange and extracorporeal carbon dioxide removal. Such device often have one or more sensor modules that measure one or more characteristics (for example, pressure and/or flow rate) of the media (for example, blood) being delivered.

To prevent contamination when using such a device on multiple patients, biosafety protocols require replacement of consumable (i.e., one-time use, disposable) components (for example, tubing) and thorough cleaning of reusable components (for example, the device itself) after each use of the device. Many such devices use one or more disposable, one-time use sensor modules. Such sensor modules typically need to communicate with the device itself, such as to enable the device to monitor and adjust the pressure of the flowing media and are therefore typically electrically connected to the device when in use.

After the device is used and the consumable components (including the sensor module(s)) are removed and discarded, the device itself needs to be thoroughly cleaned. Such a cleaning typically involves the use of a cleaning solution. However, it is important that such a cleaning solution not enter the device during the cleaning process, as the cleaning solution may damage the internal components of the device. Some types of electrical connections between a sensor module and a device may undesirably provide an opening to the interior of the device through which the cleaning solution could enter.

Embodiments of the present disclosure provide a device for delivering at least one flowing media and associated sensor module that can be mechanically and electrically connected to and disconnected from the device, and which provide an electrical connection mechanism that is fluid-resistant when the sensor module is removed from the device, thereby enabling cleaning of the device without the cleaning solution entering the device at the point of electrical connection of the sensor module to the device. Embodiments of the present disclosure may be used with any such device for delivering at least one flowing media having an associated component that is mechanically and electrically connected for use and disconnected after use.

To address challenges and limitations associated with devices for delivering at least one flowing media, various examples of the present disclosure may be provided. For example, various examples of the present disclosure may provide example devices for delivering at least one flowing media, associated sensor modules, and associated methods. In various embodiments, the present disclosure may provide a device for delivering at least one flowing media and an associated sensor module or cartridge that is selectively mechanically and electrically connectable to and removable from the device.

Figure 2:
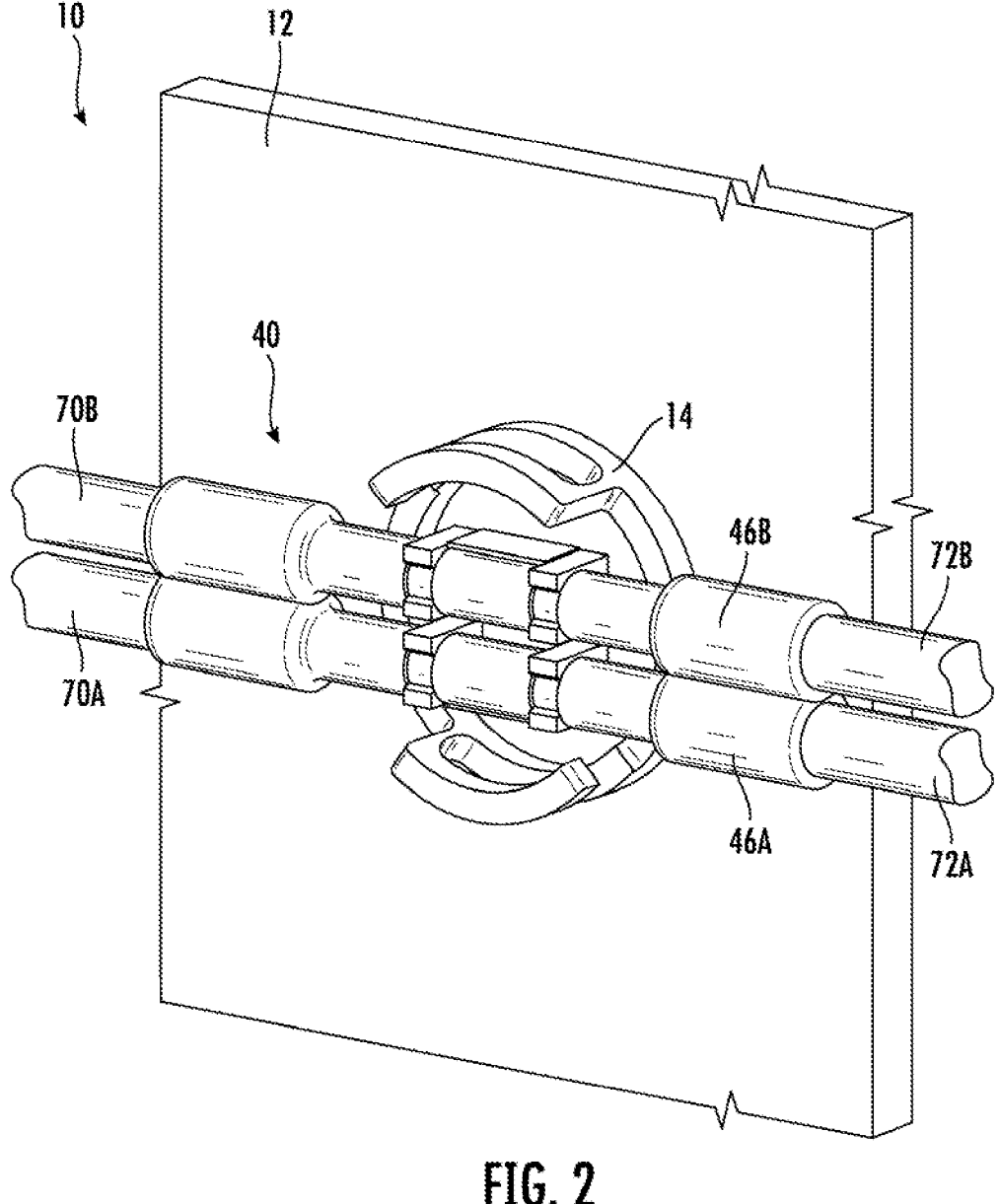
FIG. 2 is a front perspective view of the device of FIG. 1, showing the sensor module positioned for attachment.
Figure 3:
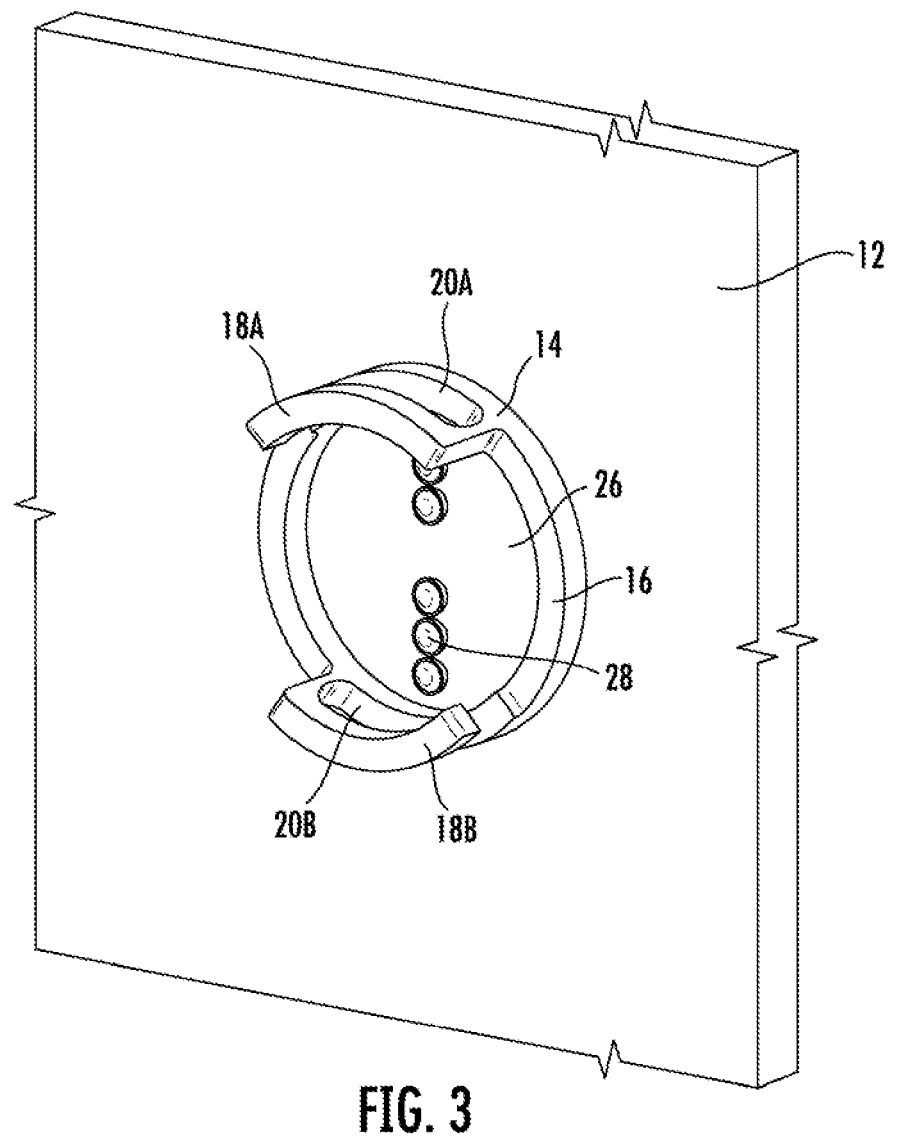
FIG. 3 is a front perspective view of the device of FIG. 1, with the sensor module removed.
Figure 4:
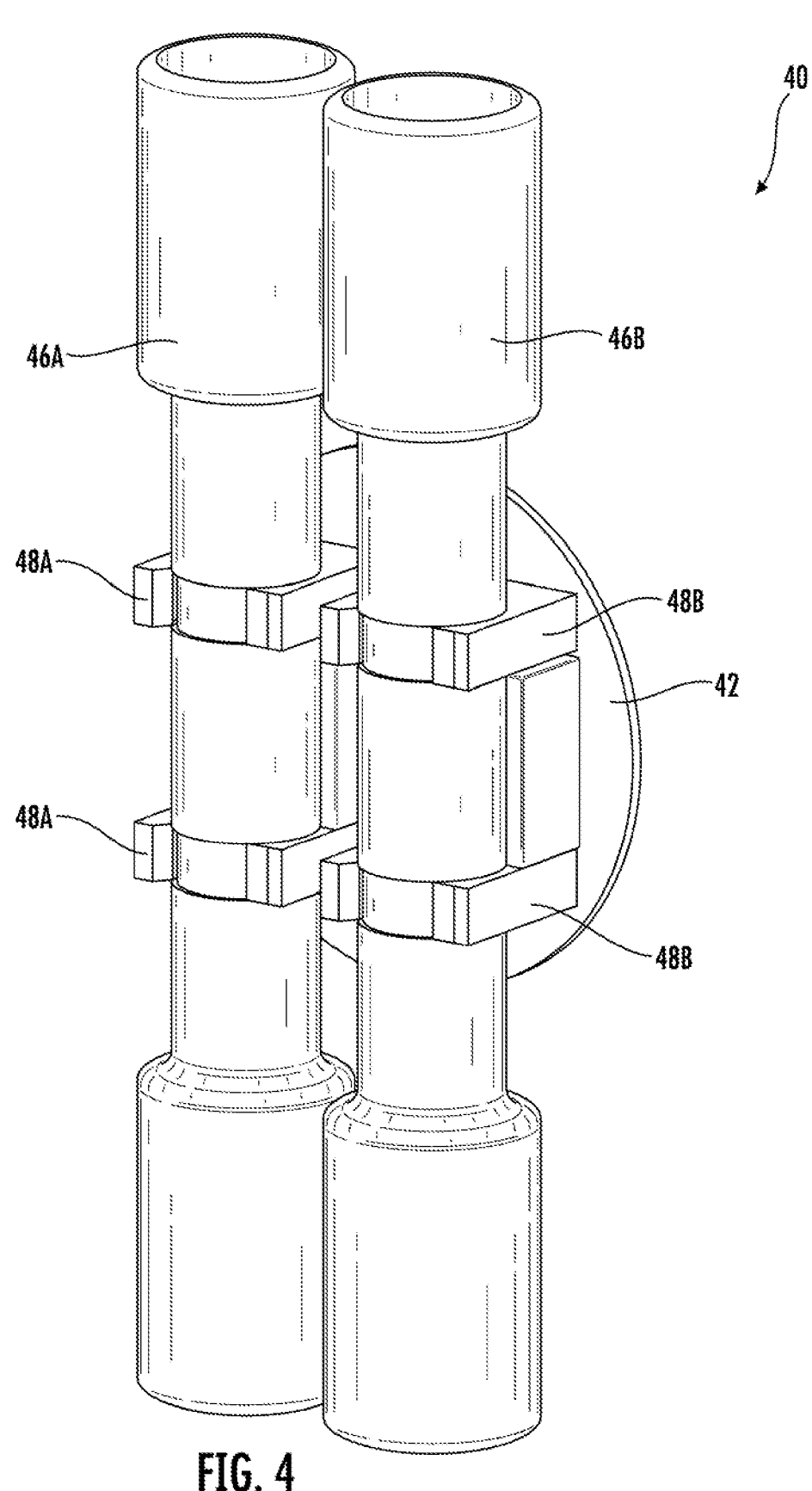
FIG. 4 is a front perspective view of the sensor module of FIG. 1, removed from the device.
Figure 5:
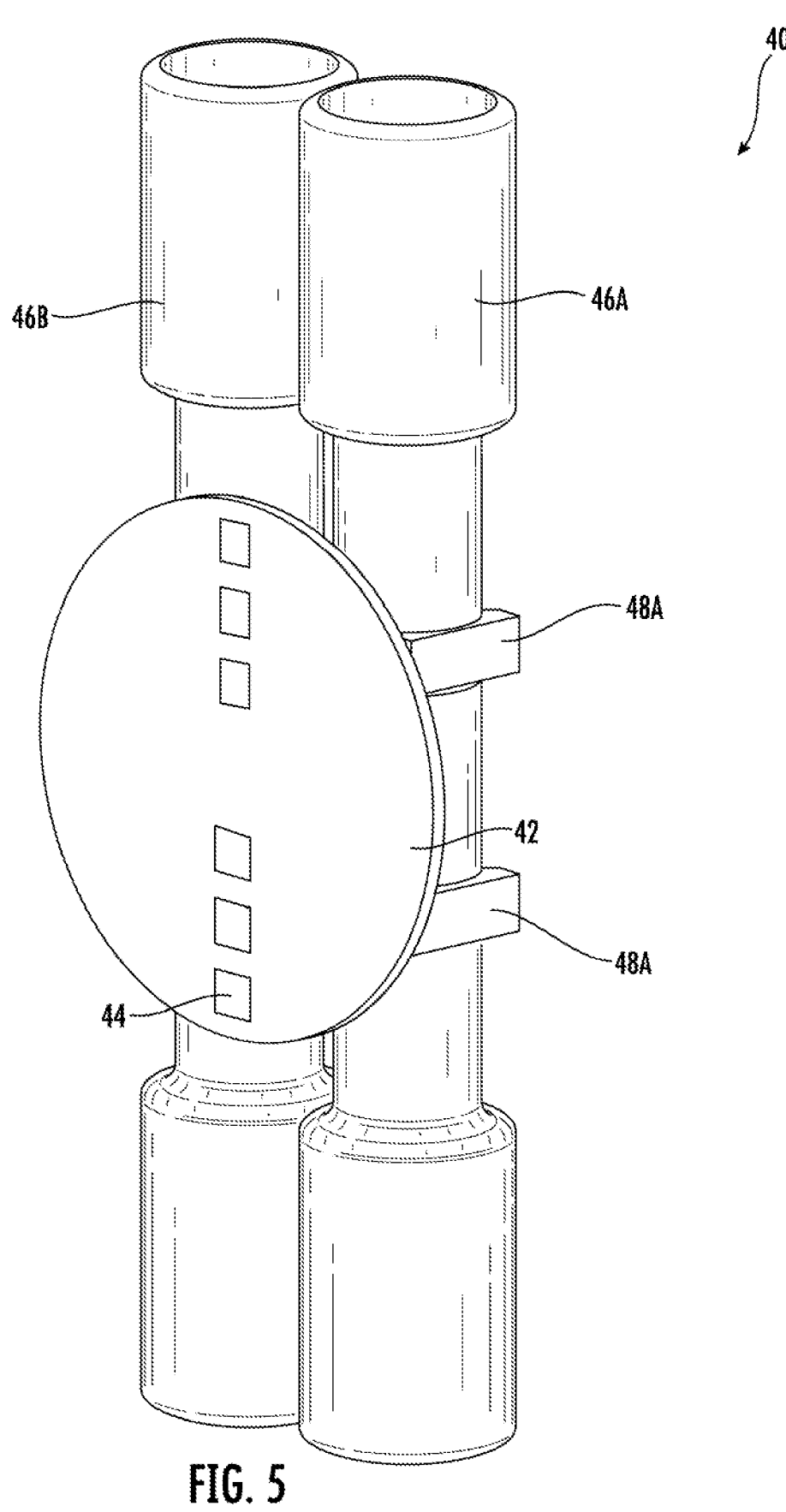
FIG. 5 is a rear perspective view of the sensor module of FIG. 1, removed from the device.

Referring now to FIGS. 1-5 and 7, a portion of an example device 10 for delivering at least one flowing media is illustrated, in accordance with various embodiments of the present disclosure. FIG. 1 illustrates the example device 10 with an example sensor module 40 mechanically and electrically connected to the device 10 for use. FIG. 2 illustrates the example device 10 with the example sensor module 40 positioned to be mechanically and electrically connected to the device 10. FIG. 3 illustrates the example device 10 with the example sensor module 40 removed from the device 10. FIGS. 4 and 5 illustrate the example sensor module 40 removed from the device 10.

In some embodiments, the device 10 for delivering at least one flowing media comprises a housing 12. In some embodiments, the housing holds various internal components of the device 10, such as one or more printed circuit board assemblies (PCBAs), one or more pumps, one or more power supplies, etc.

Figure 7:
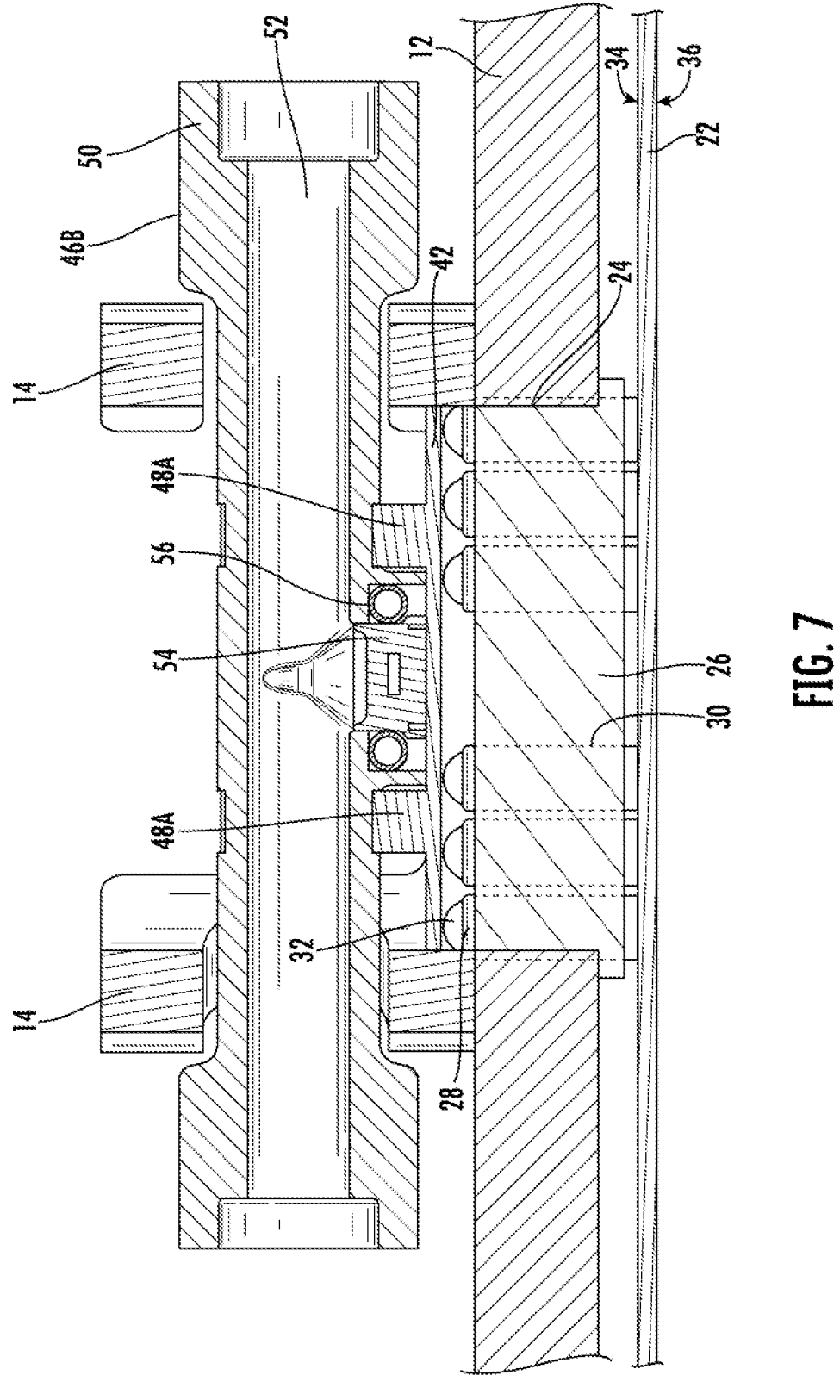
FIG. 7 is a sectional view of the device and sensor module of FIG. 1, along line 7-7 in FIG. 1.

In some embodiments, the housing 12 defines an opening 24 (seen in FIG. 7) at the location where the sensor module 40 is selectively attachable to the device 10. In some embodiments, the device 10 includes a fluid-resistant seal 26 that is positioned to occlude the opening 24. The fluid-resistant seal 26 may be constructed of any suitable material that is sufficiently durable and resistant to one or more cleaning solutions typically used in a healthcare facility. In some embodiments, the fluid-resistant seal 26 is constructed of a resilient material that is sized to fit snugly within the opening 24 to help prevent any fluid from entering the housing 12 at the edge of the fluid-resistant seal 26. In some embodiments, the fluid-resistant seal 26 is constructed of a moldable material. In some embodiments, the fluid-resistant seal 26 is constructed of silicone. In some embodiments, the fluid-resistant seal 26 is constructed of fluorosilicone. In some embodiments, as seen in FIG. 7, the fluid-resistant seal 26 has a wide base that helps retain the fluid-resistant seal 26 in the opening 24.

In some embodiments, the device 10 for delivering at least one flowing media comprises a first printed circuit board assembly (PCBA) 22 disposed within the housing. In some embodiments, the first PCBA 22 has a first major surface 34 and an opposing second major surface 36. In some embodiments, the first PCBA 22 is positioned adjacent the opening 24 with the first major surface 34 toward the opening 24.

The example first PCBA 22 may comprise a thick film printed ceramic board, a laminate, and/or other material. The example first PCBA 22 may comprise an FR4 substrate. In various embodiments, the example first PCBA 22 may comprise epoxy, ceramic, alumina, LCPs, and/or the like.

The example first PCBA 22 may comprise one or more electronic components thereon and/or pads for connecting to other electronic components of the device 10 for delivering at least one flowing media and/or other apparatuses. In some examples, the first PCBA 22 may include an application specific integrated circuit (ASIC) that may be attached to a surface of the first PCBA 22, such as an ASIC electrically coupled to the first PCBA 22 via wire bonds, bump bonds, electrical terminals, and/or any other suitable electrical connections. In various embodiments, the ASIC converts the millivolt/ratio metric output from a sensing element of a sensor module (described further below) into digital counts, using stored coefficients for the mathematical calculations related to the conversion. In some examples, the first PCBA 22 may include a microcontroller that may be attached to a surface of the first PCBA 22, such as a microcontroller electrically coupled to the first PCBA 22 via wire bonds, bump bonds, electrical terminals, and/or any other suitable electrical connections. In various embodiments, the microcontroller contains instructions for adjustments/corrections to the data from the ASIC and provides an interface to provide the data (e.g., pressure or flow rate) to circuitry external to the device 10 for delivering at least one flowing media. Additionally or alternatively, the example first PCBA 22 may include one or more conductive pads, connectors, and/or the like for engaging circuitry and/or electronic components in communication with a remote processor or the like.

In various examples, the first PCBA 22 may comprise one or more processing electronics and/or compensation circuitry (e.g., which may or may not include an ASIC). Such processing electronics may be electrically connected (as described herein, via the fluid-resistant seal) to terminals of the sensing element, an ASIC (if present), and/or electrical terminals to process electrical signals from the example sensing element and/or to transfer outputs from the example sensing element to electronic components of one or more apparatuses used in conjunction with the device 10 for delivering at least one flowing media. In some instances, the first PCBA 22 may include circuitry that may be configured to format one or more output signals provided by the example sensing element into a particular output format. For example, circuitry of the first PCBA 22 may be configured to format the output signal provided by the example sensing element into a ratio-metric output format, a current format, a digital output format and/or any other suitable format. In some cases, the circuitry of the first PCBA 22 may be configured to provide an output to one or more electrical terminals facilitating electrical connections with electronic components of one or more apparatuses used in conjunction with the device 10 for delivering at least one flowing media.

In some embodiments, the device 10 for delivering at least one flowing media comprises a twist-lock mechanism 14 to enable selective mechanical attachment of the sensor module 40 to the device 10. As best seen in FIG. 3, the twist-lock mechanism 14 comprises a circular base 16 defining an opening that is aligned with the opening 24 in the housing 12 and therefore provides access to the fluid-resistant seal 26. In some embodiments, the twist-lock mechanism 14 is securely affixed to the housing 12 to prevent the twist-lock mechanism 14 from rotating when the sensor module is rotated into engagement with the twist-lock mechanism 14. In some embodiments, the twist-lock mechanism has a projecting tab or the like (not illustrated) that engages with a corresponding slot or the like (not illustrated) on the housing to help prevent the twist-lock mechanism from rotating. Alternatively, the housing may have a projecting tab or the like (not illustrated) that engages with a corresponding slot or the like (not illustrated) on the twist-lock mechanism to help prevent the twist-lock mechanism from rotating. In some embodiments, a sealant and/or adhesive (not illustrated) helps secure the twist-lock mechanism to the housing and helps prevent any fluid ingress around the fluid-resistant seal. In the illustrated embodiment, the twist-lock mechanism 14 further comprises opposing first and second arms 18A, 18B that project outward from the base 16. In the illustrated embodiment, each of the opposing first and second arms 18A, 18B of the twist-lock mechanism 14 define a respective channel 20A, 20B, respectively. In the illustrated embodiment, each of the channels 20A, 20B have an open end facing in an opposite direction from the open end of the other channel, thereby enabling the twist-lock connection of the sensor module 40 to the device 10 as described further below. In alternative embodiments of the disclosure, other types of mechanical attachment mechanisms may be used to enable mechanical attachment of the sensor module 40 to the device 10. For example, in some embodiments, one or more snaps, clips, and/or the like may be used to mechanically attach the sensor module to the device.

In some embodiments, the sensor module 40 comprises a second printed circuit board assembly (PCBA) 42 having a first major surface 80 and an opposing second major surface 82. In some embodiments, the second major surface 82 has a plurality of electrical contact pads 44. The example second PCBA 42 may comprise a thick film printed ceramic board, a laminate and/or other material. The example second PCBA 42 may comprise an FR4 substrate. In various embodiments, the example second PCBA 42 may comprise epoxy, ceramic, alumina, LCPs, and/or the like.

In some embodiments, the sensor module 40 comprises one or more flow tubes (first and second flow tubes 46A, 46B are illustrated) attached to the second PCBA 42. In some embodiments, each of the first and second flow tubes 46A, 46B defines a flow path 52 for conveying a flowing media therethrough. In an example embodiment in which the device is a dialysis machine, one of the flow tubes may define a flow path through the sensor module for blood from the patient to a filter and the other of the flow tubes may define a flow path through the sensor module for blood from the filter back to the patient.

Figure 10:
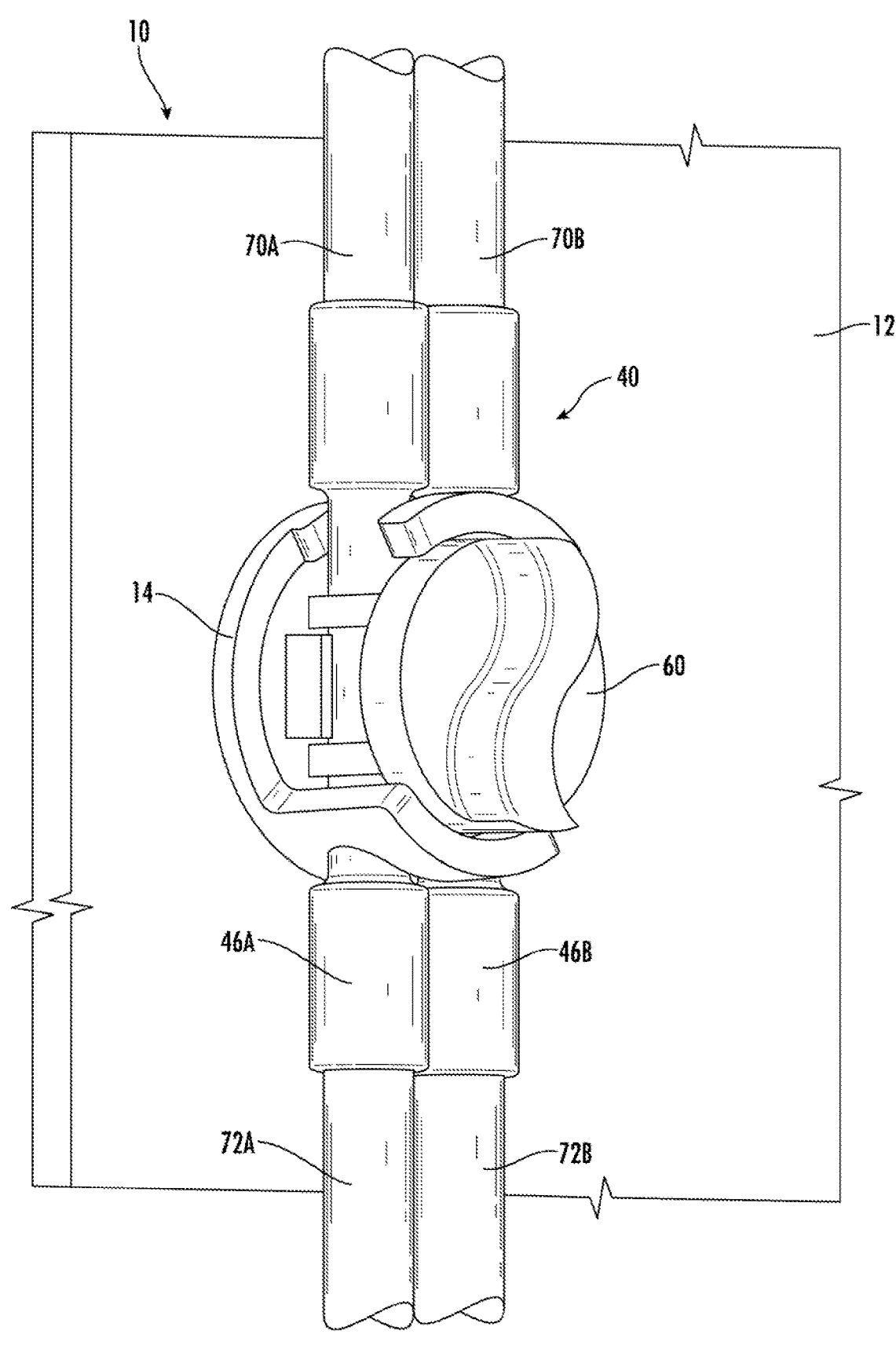
FIG. 10 is a front perspective view of the grasping handle of FIGS. 8 and 9, attached to the sensor module of FIG. 1.

As seen in FIGS. 1, 2 and 10, during use and in preparation for use of the device 10 for delivering at least one flowing media, tubing is attached to both ends of the flow tube(s). In the illustrated embodiment, first patient-side tubing 70A is attached to a first end of the first flow tube 46A, second patient-side tubing 70B is attached to a first end of the second flow tube 46B, first machine-side tubing 72A is attached to a second end of the first flow tube 46A, and second machine-side tubing 72B is attached to a second end of the second flow tube 46B. In an example embodiment, blood travels from the patient to the sensor module via the first patient-side tubing 70A, blood travels from the sensor module to the filter of the device via the first machine-side tubing 72A, blood travels from the filter of the device to the sensor module via the second machine-side tubing 72B, and blood travels from the sensor module to the patient via the second patient-side tubing 70B. In the illustrated embodiment, the connection type between the tubing and the sensor module is a socket fitting. Any type of connection type between the tubing and the flow tubes may be used, such as but not limited to barbed fittings, Luer-Lock fittings, Swage-Lock fittings, and/or the like.

In some embodiments, the sensor module 40 comprises one or more sensing elements 54 (e.g., sense die, transducer and/or the like) disposed on the first major surface 80 of the second PCBA 42. In some embodiments, the sensing element 54 may comprise a micro-electromechanical system (MEMS) die. In some embodiments with more than one flow tube, there is a sensing element associated with each flow tube. In some embodiments, the sensing element 54 is in electrical communication with one or more of the plurality of electrical contact pads 44. In some embodiments with more than one flow tube, the sensing element associated with each flow tube is in electrical communication with a different one or more of the plurality of electrical contact pads 44. In various embodiments, the sensing element 54 produces a millivolt output in relation to the pressure of the flowing media within the flow path. In various examples, the sensing element 54 may be electrically connected to the second PCBA 42 using various techniques. For example, the sensing element 54 may be electrically connected to its own PCBA which is in turn electrically connected (e.g., soldered) to the second PCBA 42. As another example wire bonds, bump bonds, or the like may be utilized to electrically connect the example sensing element 54 to the second PCBA 42.

Each flow tube comprises an elongated main body 50 disposed proximate the first major surface of the second PCBA 42 such that the flow path is disposed proximate the respective sensing element 54 and at least a portion of the flowing media through the flow tube makes direct contact with the sensing element 54 or indirect contact with the sensing element 54, such as via a gel covering (not illustrated) at least a portion of the sensing element 54. In some embodiments, such a gel covering is used to help prevent contamination of the flowing media. As seen in FIG. 7, the sensing element 54 extends into the body 50 of the flow tube 46A, and an O-ring 56 prevents leakage of the flowing media around the sensing element. In some embodiments, a sealant, epoxy (such as a UV-curable epoxy), and/or the like (not illustrated) may be used in place of the O-ring.

In some embodiments, the extension of each sensing element 54 into the body 50 of each flow tube, along with the O-ring 56, provides a mechanical coupling of each flow tube to the sensing element and therefore to the second PCBA 42. This mechanical coupling may be subjected to significant torque when the sensor module 40 is rotated to engage with the twist-lock mechanism 14, such that this mechanical coupling alone may not be sufficient to retain the flow tube(s) to the second PCBA 42. Thus, in some embodiments, additional attachment mechanisms are used to mechanically couple the flow tube(s) to the second PCBA 42. In the illustrated embodiment, first clips 48A retain the first flow tube 46A to the second PCBA 42 and second clips 48B retain the second flow tube 46B to the second PCBA 42. In the illustrated embodiment, the clips for each respective flow tube are positioned on opposite sides of the respective sensing element.

As described above, in some embodiments the sensor module is selectively attachable to the device. In the illustrated embodiment, the sensor module 40 is selectively attachable to the device 10 via a twist-lock mechanism 14. To selectively attach the sensor module 40 to the device 10, the sensor module 40 is positioned such that the second PCBA 42 of the sensor module 40 is aligned with the fluid-resistant seal 26 and such that the flow tubes fit between the first arm 18A and the second arm 18B of the twist-lock mechanism 14, as seen in FIG. 2. In some embodiments, the sensor module 40 is then rotated such that portions of the flow tubes 46A, 46B enter the channel 20A of the first arm 18A of the twist-lock mechanism 14 and different portions of the flow tubes 46A, 46B enter the channel 20B of the second arm 18B of the twist-lock mechanism 14. In some embodiments, when the sensor module 40 has been rotated as much as possible (that is, one of the flow tubes contacts the closed end of one of the channels and the other of the flow tubes contacts the closed end of the other of the channels), the sensor module 40 is securely mechanically coupled to the device 10. In some embodiments, the distal ends of each of the second arms 18A, 18B have a protrusion (not illustrated) projecting into each respective channel 20A, 20B to help retain the flow tubes 46A, 46B in the channels 20A, 20B.

In some embodiments, prior to rotating the sensor module 40, the sensor module 40 is pushed firmly against the device 10. In some embodiments, pushing the sensor module 40 firmly against the device 10 helps ensure the electrical connection between the sensor module 40 and the device 10, as described further below.

In some embodiments, an electrical connection between the sensor module 40 and the device 10 (specifically with the first PCBA 22 of the device 10, in the illustrated example embodiment) is completed when the sensor module 40 is mechanically attached to the device 10 (as described below). In some embodiments, the electrical connection between the sensor module 40 and the device 10 is made via the fluid-resistant seal 26.

In some embodiments, as seen in FIGS. 3 and 7, a plurality of electrical connectors are connected to the first PCBA 22 in the housing 12 and extend through the fluid-resistant seal 26. In the illustrated embodiment, the plurality of electrical connectors are spring-loaded pins 28 (which are also termed pogo pins). The illustrated embodiment has six spring-loaded pins 28, but any suitable number may be used. In the illustrated embodiment, the spring-loaded pins 28 are in a linear arrangement. In some embodiments, such a linear arrangement is preferable because it ensures that the electrical connection between the sensor module and the device is not completed until the sensor module is fully mechanically coupled to the device, as described further below.

The spring-loaded pins 28 each comprise a barrel 30 which is embedded in the fluid-resistant seal 26 and a plunger 32 which extends outwardly from the fluid-resistant seal 26. The plunger 32 of each of the spring-loaded pins 28 is biased outwardly along the longitudinal axis of the barrel 30. In some embodiments, the fluid-resistant seal 26 is molded around the spring-loaded pins 28. In some embodiments, the fluid-resistant seal 26 is constructed with a number of through-holes corresponding to the number of spring-loaded pins, and each of the spring-loaded pins are inserted into a respective through-hole. In such an embodiments in which the spring-loaded pins are inserted into respective through-holes, the through-holes are sized such that the spring-loaded pins fit snugly within each respective through-hole to prevent the intrusion of cleaning solution around the spring-loaded pins.

In some embodiments, when the sensor module 40 is mechanically attached to the device 10 as described above, each of the contact pads 44 of the second PCBA 42 contact a respective one of the spring-loaded pins 28, thereby completing an electrical connection between the second PCBA 42 and the first PCBA 22. In some embodiments, this electrical connection between the second PCBA 42 and the first PCBA 22 enables the sensor module 40 to function with the device 10. In some embodiments, this electrical connection between the second PCBA 42 and the first PCBA 22 enables electrical signals from the second PCBA 42 to the first PCBA 22 and vice versa. In some embodiments, this electrical connection between the second PCBA 42 and the first PCBA 22 enables electrical power to be provided from the first PCBA 22 to the second PCBA 42, such that the sensor module 40 does not require its own independent power supply.

In some embodiments, such as the linear arrangement of the spring-loaded pins 28 shown in FIG. 7 and the shape/size/arrangement of the contact pads 44 shown in FIG. 5, the electrical connection between the second PCBA 42 and the first PCBA 22 is not completed until the sensor module 40 is fully mechanically coupled to the device 10. In such an embodiment, it is only when the sensor module 40 is fully mechanically coupled to the device that the contact pads 44 align with and contact the respective spring-loaded pins 28 to complete the electrical connection.

Figure 6:
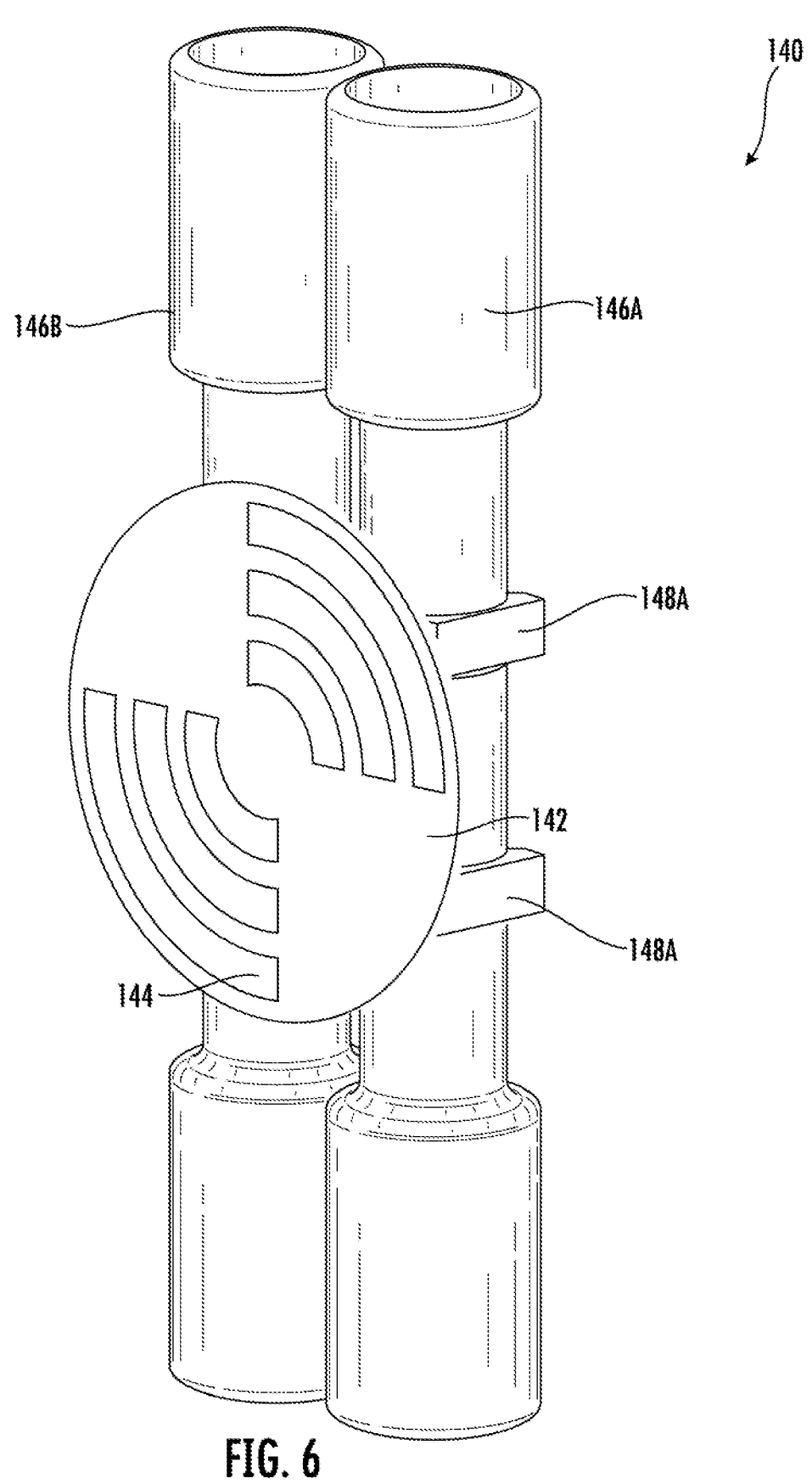
FIG. 6 is a rear perspective view of an example sensor module for use with an example device for delivering at least one flowing media, in accordance with some alternative embodiments of the present disclosure.

In some contexts, there may be some concern that moving the contact pads into contact with the spring-loaded pins when rotating the sensor module into engagement with the twist-lock mechanism could mechanically damage the leading edges of the contact pads. FIG. 6 illustrates an alternative sensor module that addresses such concerns. FIG. 6 illustrates a sensor module 140 comprising first and second flow tubes 146A, 146B attached via first and second clips (only the first clips 148A are visible in FIG. 6) to a PCBA 142. The PCBA 142 has a plurality of contact pads 144. The contact pads 144 of the PCBA 142 of the alternative sensor module 140 are arcuate. Due to the arcuate shape of the contact pads 144, the contact pads 144 are in contact with the respective spring-loaded pins 28 during the entire time the sensor module 140 is being rotated into engagement with the twist-lock mechanism 14 (i.e., in the position shown in FIG. 2, while rotating from the position shown in FIG. 2 into the position shown in FIG. 1, and in the position shown in FIG. 1). In this embodiment, since the contact pads 144 are in contact with the respective spring-loaded pins 28 during the entire time the sensor module 140 is being rotated into engagement with the twist-lock mechanism 14, there is no risk of damaging the leading edges of the contact pads.

Figure 8:
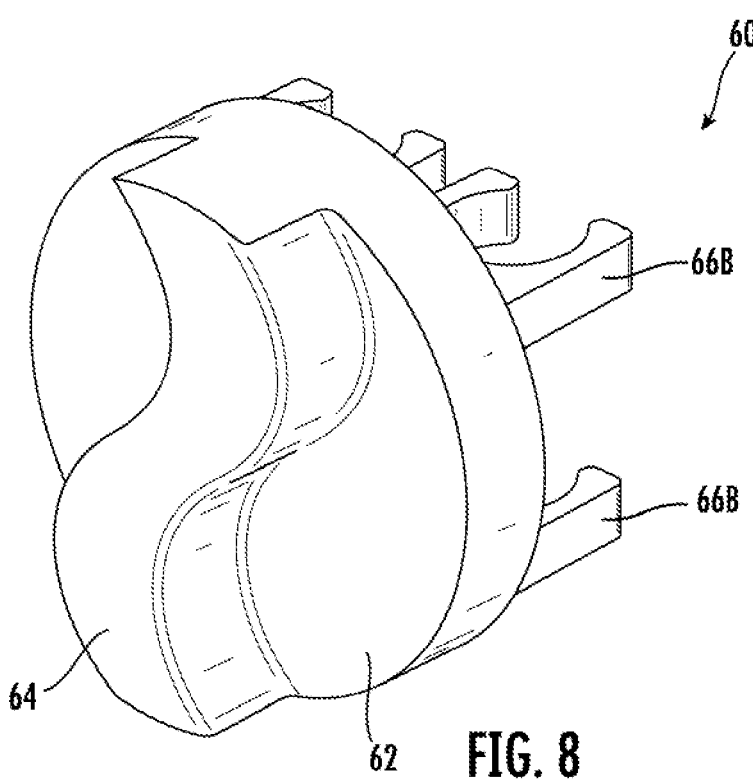
FIGS. 8 and 9 are, respectively, front and rear perspective views of an example grasping handle for use with an example sensor module, in accordance with some embodiments of the present disclosure.
Figure 9:
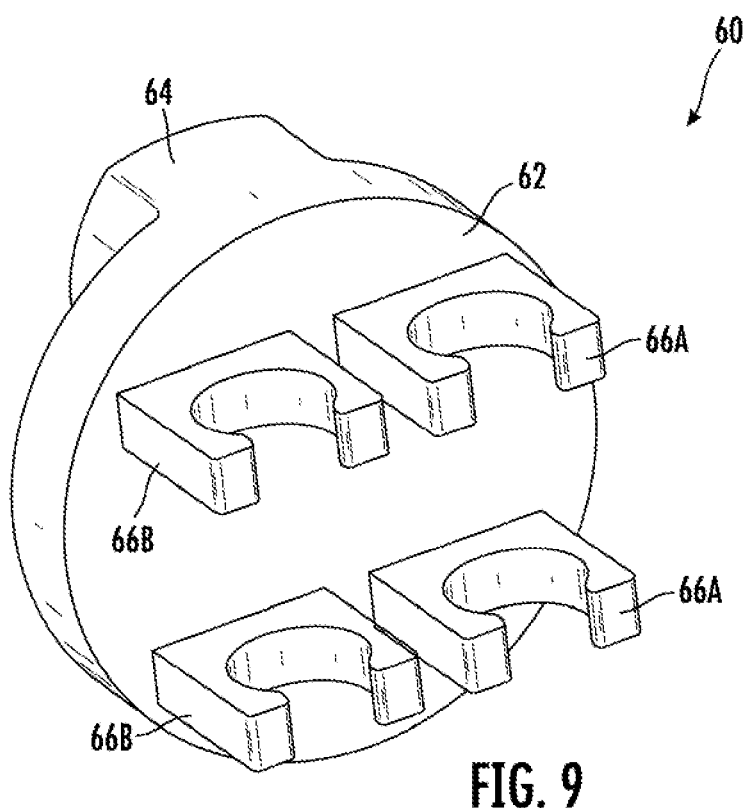

As seen in FIG. 2, in some embodiments there is little clearance between the flow tubes and the twist-lock mechanism. As such, when engaging and disengaging the sensor module with the twist-lock mechanism, it may be challenging for a user to firmly grasp the sensor module to rotate the sensor module into and out of engagement with the twist-lock mechanism. To assist a user with grasping the sensor module to rotate the sensor module into and out of engagement with the twist-lock mechanism, in some embodiments a grasping handle is provided that is selectively attachable to the sensor module. Referring now to FIGS. 8-10, an example grasping handle 60 comprises a main body 62, a raised grasping portion 64, and first and second mounting clips 66A, 66B. As seen in FIG. 10, in some embodiments the grasping handle 60 is selectively attachable to the sensor module. In the illustrated embodiment, the grasping handle 60 is selectively attachable to the sensor module by simultaneously engaging the first mounting clips 66A with the first flow tube 46A and the second mounting clips 66B with the second flow tube 46B, such as by aligning the mounting clips 66A, 66B with the respective flow tubes 46A, 46B and pushing the grasping handle 60 against the flow tubes. With the grasping handle 60 selectively attached to the sensor module 40, a user can readily hold and turn the sensor module 40 to attach the sensor module to the device using the grasping handle 60. In some embodiments, the grasping handle 60 can be left attached to the sensor module 40 during operation of the device, thereby enabling the grasping handle 60 to be used to detach the sensor module from the device after use. In some embodiments, as illustrated, the main body 62 is circular and sized to fit within the first and second arms 18A, 18B of the twist-lock mechanism 14 when the sensor module is attached to the device to provide a lower profile. In some embodiments, as illustrated, the raised grasping portion 64 is a raised ridge projecting outwardly from the main body 62. In some embodiments, the grasping handle may be discarded along with the sensor module after use. In some embodiments, the grasping handle may be detached from the sensor module after use, cleaned, and re-used.

Figure 11:
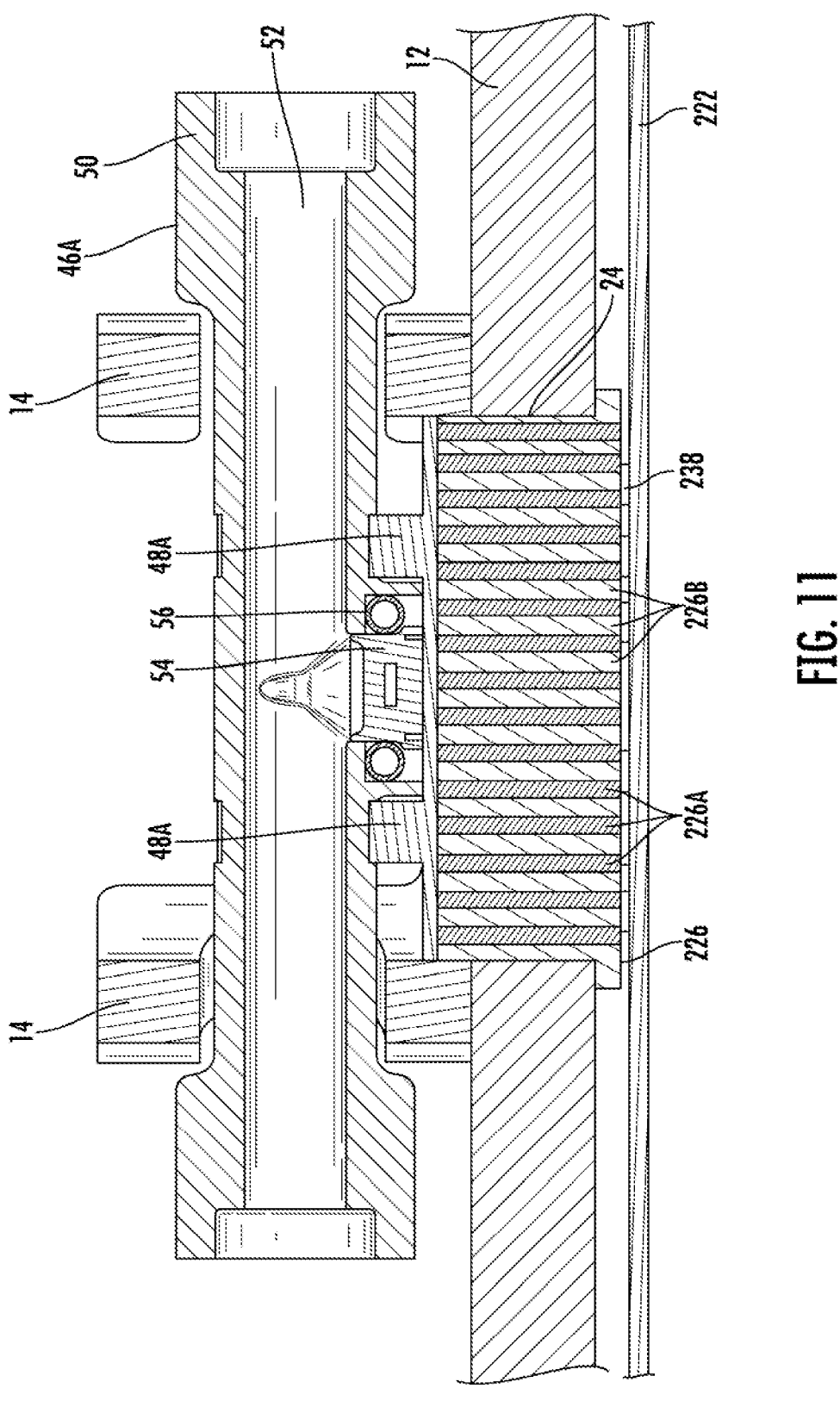
FIG. 11 is a sectional view of an example device for delivering at least one flowing media, with an attached sensor module, in accordance with some alternative embodiments of the present disclosure.

Referring now to FIG. 11, a sectional view of an example device for delivering at least one flowing media, with an attached sensor module, is illustrated in accordance with some alternative embodiments of the present disclosure. The device of FIG. 11 is very similar to the device of FIG. 7, however, in FIG. 11 the fluid-resistant seal and spring-loaded pins have been replaced by a compressibly-conductive fluid-resistant seal 226 (which may also be termed a compression-type electrically conductive seal). In some embodiments, the compressibly-conductive fluid-resistant seal 226 is a Z-axis conductive elastomeric inter-connector, such as is manufactured by Shin-Etsu Polymer America, Inc. In some embodiments, the compressibly-conductive fluid-resistant seal 226 comprises a plurality of compressibly-conductive Z-axis columns 226A and a plurality of non-conductive Z-axis columns 226B interspersed throughout the full thickness of an elastomeric material (for example, silicone or fluorosilicone). In some embodiments, the compressibly-conductive Z-axis columns 226A comprise a plurality of conductive particles (for example, metal or carbon fiber) embedded in Z-axis columns in the compressibly-conductive fluid-resistant seal 226. In some embodiments, when the compressibly-conductive fluid-resistant seal 226 is compressed along its Z-axis, the conductive particles in each of the Z-axis columns move together to create a conductive path along the Z-axis column from one side of the compressibly-conductive fluid-resistant seal 226 to the opposing side of the compressibly-conductive fluid-resistant seal 226.

In some embodiments, as illustrated in FIG. 11, the compressibly-conductive fluid-resistant seal 226 projects outwardly beyond the outer surface of the housing 12. In some embodiments, because of this outward projection the second PCBA 42 of the sensor module pushes against and compresses the compressibly-conductive fluid-resistant seal 226 when the sensor module is attached to the device. In some embodiments, as illustrated in FIG. 11, the first PCBA 222 within the housing 12 has a plurality of contact pads 238 on the major surface facing the housing 12. When the sensor module is attached to the device, the compressibly-conductive fluid-resistant seal 226 is compressed between the first PCBA 222 and the second PCBA 42 and an electrical connection is formed between one or more of the contact pad 238 of the first PCBA 222 and one or more respective contact pad 44 of the second PCBA 42.

While the description above provides an example device 10 for delivering at least one flowing media, it is noted that the scope of the present disclosure is not limited to the description above. In some examples, an example device 10 for delivering at least one flowing media in accordance with the present disclosure may be in other forms. In some examples, a device 10 for delivering at least one flowing media may comprise one or more additional and/or alternative elements, and/or may be structured/positioned differently than illustrated herein.

Figure 12:
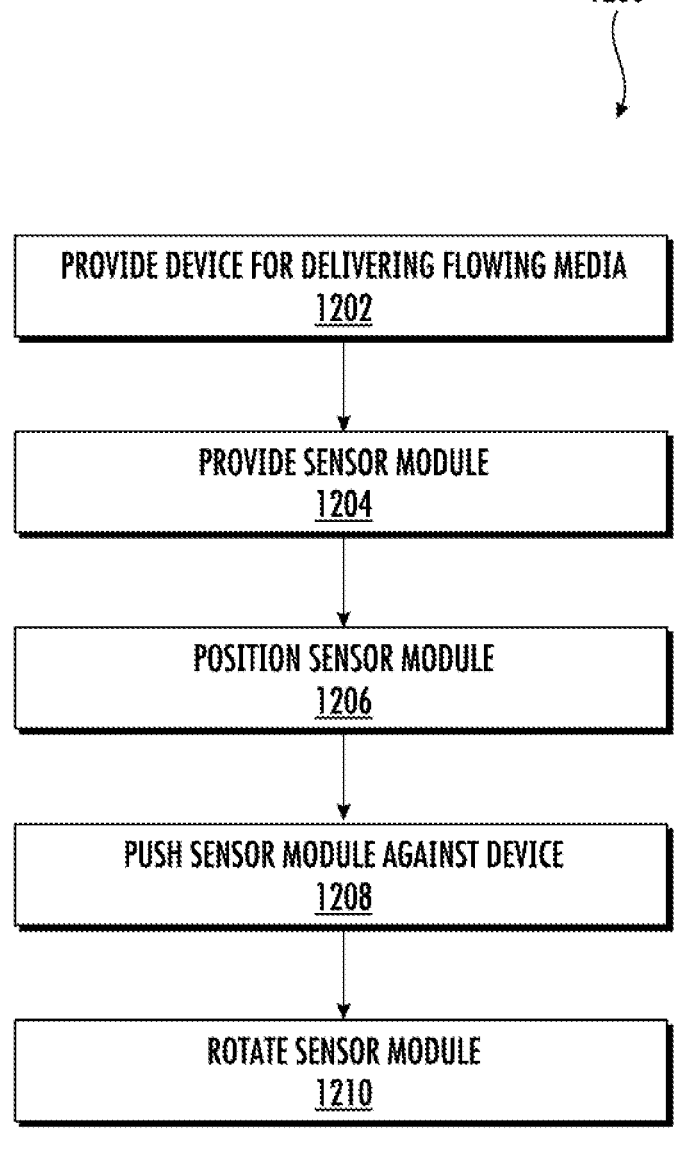
FIG. 12 is an example flowchart illustrating an example method of mechanically and electrically coupling a sensor module to a device for delivering at least one flowing media, in accordance with some embodiments of the present disclosure.

Reference will now be made to FIG. 12, which provides a flowchart illustrating example steps, processes, procedures, and/or operations in accordance with various embodiments of the present disclosure. Various methods described herein, including, for example, methods as shown in FIG. 12, may provide various technical benefits and improvements.

Referring now to FIG. 12, an example method 1200 is illustrated. In some embodiments, the example method comprises mechanically and electrically coupling a sensor module to a device for delivering at least one flowing media.

At step/operation 1202, a device for delivering at least one flowing media (such as, but not limited to, the device 10 for delivering at least one flowing media described above in connection with FIGS. 1-3 and 7) is provided.

At step/operation 1204, a sensor module (such as, but not limited to, the sensor module 40 described above in connection with FIGS. 1-5 and 7) is provided.

At step/operation 1206, the sensor module is positioned for attachment to the device for delivering at least one flowing media (such as, but not limited to, in the position described above in connection with FIG. 2).

At step/operation 1208, while in the position described in relation to step/operation 1206, the sensor module is pushed against the device for delivering at least one flowing media.

At step/operation 1210, the sensor module is rotated into engagement with the device for delivering at least one flowing media (such as, but not limited to, from the position described above in connection with FIG. 2 to the position described above in connection with FIG. 1).

Operations and processes described herein support combinations of means for performing the specified functions and combinations of operations for performing the specified functions. It will be understood that one or more operations, and combinations of operations, may be implemented by special purpose hardware-based computer systems which perform the specified functions, or combinations of special purpose hardware and computer instructions.

In some example embodiments, certain ones of the operations herein may be modified or further amplified as described below. Moreover, in some embodiments additional optional operations may also be included. It should be appreciated that each of the modifications, optional additions or amplifications described herein may be included with the operations herein either alone or in combination with any others among the features described herein.

The foregoing method and process descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," and similar words are not intended to limit the order of the steps; these words are simply used to guide the reader through the description of the methods. Further, any reference to claim elements in the singular, for example, using the articles "a," "an" or "the," is not to be construed as limiting the element to the singular and may, in some instances, be construed in the plural.

While various embodiments in accordance with the principles disclosed herein have been shown and described above, modifications thereof may be made by one skilled in the art without departing from the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present disclosure. Furthermore, any advantages and features described above may relate to specific embodiments but shall not limit the application of such issued claims to processes and structures accomplishing any or all of the above advantages or having any or all of the above features.

In addition, the section headings used herein are provided for consistency with the suggestions under 37 C.F.R. § 1.77 or to otherwise provide organizational cues. These headings shall not limit or characterize the disclosure set out in any claims that may issue from this disclosure. For instance, a description of a technology in the "Background" is not to be construed as an admission that certain technology is prior art to any disclosure in this disclosure. Neither is the "Summary" to be considered as a limiting characterization of the disclosure set forth in issued claims. Furthermore, any reference in this disclosure to "disclosure" or "embodiment" in the singular should not be used to argue that there is only a single point of novelty in this disclosure. Multiple embodiments of the present disclosure may be set forth according to the limitations of the multiple claims issuing from this disclosure, and such claims accordingly define the disclosure, and their equivalents, which are protected thereby. In all instances, the scope of the claims shall be considered on their own merits in light of this disclosure but should not be constrained by the headings set forth herein.

Also, systems, subsystems, apparatuses, techniques, and methods described and illustrated in the various embodiments as discrete or separate may be combined or integrated with other systems, modules, techniques, or methods without departing from the scope of the present disclosure. Other devices or components shown or discussed as coupled to, or in communication with, each other may be indirectly coupled through some intermediate device or component, whether electrically, mechanically, or otherwise. Other examples of changes, substitutions, and alterations are ascertainable by one skilled in the art and could be made without departing from the scope disclosed herein.

Many modifications and other embodiments of the disclosure set forth herein will come to mind to one skilled in the art to which these embodiments pertain having the benefit of teachings presented in the foregoing descriptions and the associated figures. Although the figures only show certain components of the apparatuses and systems described herein, various other components may be used in conjunction with the components and structures disclosed herein. Therefore, it is to be understood that the disclosure is not to be limited to the specific embodiments disclosed and that modifications and other embodiments are intended to be included within the scope of the appended claims. For example, the various elements or components may be combined, rearranged, or integrated in another system or certain features may be omitted or not implemented. Moreover, the steps in any method described above may not necessarily occur in the order depicted in the accompanying drawings, and in some cases one or more of the steps depicted may occur substantially simultaneously, or additional steps may be involved. Although specific terms are employed herein, they are used in a generic and descriptive sense only and not for purposes of limitation.

What is claimed is:

1. A device for delivering at least one flowing media, the device comprising:
a housing defining an opening;
a first printed circuit board assembly (PCBA) disposed within the housing;
a fluid-resistant seal occluding the opening; and
a sensor module comprising:
(i) a second printed circuit board assembly (PCBA) having a first major surface and an opposing second major surface, the second major surface having a plurality of electrical contact pads;
(ii) a sensing element disposed on the first major surface of the second PCBA and in electrical communication with one or more of the plurality of electrical contact pads; and
(iii) a flow tube at least partially defining a flow path for conveying a flowing media therethrough, the flow tube comprising an elongated main body disposed proximate the first major surface of the second PCBA such that the flow path is disposed proximate the sensing element such that at least a portion of the flowing media makes direct or indirect contact with the sensing element;
wherein the sensor module is selectively attachable to the device such that the second PCBA is aligned with the fluid-resistant seal when the sensor module is selectively attached to the device; and wherein one or more of the plurality of electrical contact pads are adapted to complete an electrical connection between the sensing element and the device via physical contact with at least a portion of the device.

2. The device of claim 1, wherein a plurality of spring-loaded electrical connector pins are disposed in the fluid-resistant seal such that a first end of each of the plurality of spring-loaded electrical connector pins is positioned outside of the housing and a second end of each of the plurality of spring-loaded electrical connector pins is electrically connected to the first PCBA; and
wherein the electrical connection between the sensing element and the device is completed via contact by each of the plurality of electrical contact pads with the first end of a corresponding one of the plurality of spring-loaded electrical connector pins.

3. The device of claim 2, wherein one or more of the plurality of electrical contact pads are arcuate.

4. The device of claim 1, wherein the plurality of electrical contact pads is a first plurality of electrical contact pads;
wherein the first PCBA comprises a second plurality of electrical contact pads;
wherein the fluid-resistant seal comprises a compression-type electrically conductive membrane; and
wherein the electrical connection between the sensing element and the device is completed via contact by each of the first plurality of electrical contact pads with the compression-type electrically conductive seal and contact by each of the second plurality of electrical contact pads with the compression-type electrically conductive seal.

5. The device of claim 1, wherein the sensor module is selectively attachable to the device via a twist-lock mechanism.

6. The device of claim 5, further comprising a grasping handle selectively attachable to the sensor module to enable a user to rotate the sensor module to engage the twist-lock mechanism.

7. The device of claim 1, wherein the flow tube is affixed to the second PCBA via a first connector and a second connector, the first and second connectors being affixed to the second PCBA on opposing sides of the sensing element.

8. The device of claim 1, wherein the sensing element is a first sensing element;
wherein the flow tube is a first flow tube;
wherein the flow path is a first flow path;
wherein the flowing media is a first flowing media; and
wherein the sensor module further comprises:
a second sensing element disposed on the first major surface of the second PCBA and in electrical communication with one or more of the plurality of electrical contact pads; and
a second flow tube at least partially defining a second flow path for conveying a second flowing media therethrough, the second flow tube comprising an elongated main body disposed substantially parallel to the first flow tube and proximate the first major surface of the second PCBA such that the second flow path is disposed proximate the second sensing element such that at least a portion of the second flowing media makes direct or indirect contact with the second sensing element.

9. A sensor module comprising:

a printed circuit board assembly (PCBA) having a first major surface and an opposing second major surface, the second major surface having a plurality of electrical contact pads;

a sensing element disposed on the first major surface of the PCBA and in electrical communication with one or more of the plurality of electrical contact pads; and a flow tube at least partially defining a flow path for conveying a flowing media therethrough, the flow tube comprising an elongated main body affixed to the first major surface of the PCBA such that the flow path is disposed proximate the sensing element such that at least a portion of the flowing media makes direct or indirect contact with the sensing element;

wherein one or more of the plurality of electrical contact pads are adapted to complete an electrical connection between the sensing element and a device to which the sensor module is selectively attached via physical contact with at least a portion of the device;

wherein the PCBA is configured to be aligned with a fluid-resistant seal when the sensor module is selectively attached to the device via a twist-lock mechanism;

wherein the sensor module is selectively removable from the device via the twist-lock mechanism; and wherein the fluid-resistant seal comprises a compression-type electrically conductive membrane.

10. The sensor module of claim 9, wherein one or more of the plurality of electrical contact pads are arcuate.

11. The sensor module of claim 9, further comprising a grasping handle selectively attachable to the sensor module to enable a user to rotate the sensor module to engage the twist-lock mechanism.

12. The sensor module of claim 9, wherein the flow tube is affixed to the PCBA via a first connector and a second connector, the first and second connectors being affixed to the PCBA on opposing sides of the sensing element.

13. The sensor module of claim 9, wherein the sensing element is a first sensing element;

wherein the flow tube is a first flow tube;

wherein the flow path is a first flow path;

wherein the flowing media is a first flowing media; and wherein the sensor module further comprises:

a second sensing element disposed on the first major surface of the PCBA and in electrical communication with one or more of the plurality of electrical contact pads; and a second flow tube at least partially defining a second flow path for conveying a second flowing media therethrough, the second flow tube comprising an elongated main body disposed substantially parallel to the first flow tube and proximate the first major surface of the PCBA such that the second flow path is disposed proximate the second sensing element such that at least a portion of the second flowing media makes direct or indirect contact with the second sensing element.

14. A method for mechanically and electrically coupling a sensor module to a device for delivering at least one flowing media, the method comprising:

providing a device for delivering at least one flowing media, the device comprising:

(i) a housing defining an opening;

(ii) a first printed circuit board assembly (PCBA) disposed within the housing;

(iii) a fluid-resistant seal occluding the opening; and (iv) first and second twist-lock arms proximate opposing edges of the fluid-resistant seal;

providing a sensor module comprising:

(i) a second printed circuit board assembly (PCBA) having a first major surface and an opposing second major surface, the second major surface having a plurality of electrical contact pads;

(ii) a sensing element disposed on the first major surface of the second PCBA and in electrical communication with one or more of the plurality of electrical contact pads; and (iii) a flow tube at least partially defining a flow path for conveying a flowing media therethrough, the flow tube comprising an elongated main body disposed proximate the first major surface of the second PCBA such that the flow path is disposed proximate the sensing element such that at least a portion of the flowing media makes direct or indirect contact with the sensing element;

positioning the sensor module such that the second PCBA is aligned with the fluid-resistant seal and the flow tube is insertable between the first and second twist-lock arms;

pushing the sensor module against the device; and rotating the sensor module such that at least a first portion of the flow tube is captured by the first twist-lock arm and at least a second portion of the flow tube is captured by the second twist-lock arm;

wherein one or more of the plurality of electrical contact pads complete an electrical connection between the sensing element and the device via physical contact with at least a portion of the device.

15. The method of claim 14, wherein a plurality of spring-loaded electrical connector pins are disposed in the fluid-resistant seal such that a first end of each of the plurality of spring-loaded electrical connector pins is positioned outside of the housing and a second end of each of the plurality of spring-loaded electrical connector pins is electrically connected to the first PCBA; and wherein the electrical connection between the sensing element and the device is completed via contact by each of the plurality of electrical contact pads with the first end of a corresponding one of the plurality of spring-loaded electrical connector pins.

16. The method of claim 14, wherein one or more of the plurality of electrical contact pads are arcuate.

17. The method of claim 14, wherein the plurality of electrical contact pads is a first plurality of electrical contact pads;

wherein the first PCBA comprises a second plurality of electrical contact pads;

wherein the fluid-resistant seal comprises a compression-type electrically conductive membrane; and wherein the electrical connection between the sensing element and the device is completed via contact by each of the first plurality of electrical contact pads with the compression-type electrically conductive seal and contact by each of the second plurality of electrical contact pads with the compression-type electrically conductive seal.

18. The method of claim 14, further comprising:

attaching a grasping handle to the sensor module; and grasping the grasping handle to rotate the sensor module to engage the first and second twist-lock arms.

19. The method of claim 14, wherein the sensing element is a first sensing element;

wherein the flow tube is a first flow tube;

wherein the flow path is a first flow path;

wherein the flowing media is a first flowing media;

wherein the sensor module further comprises:

a second sensing element disposed on the first major surface of the second PCBA and in electrical communication with one or more of the plurality of electrical contact pads; and a second flow tube at least partially defining a second flow path for conveying a second flowing media therethrough, the second flow tube comprising an elongated main body disposed substantially parallel to the first flow tube and proximate the first major surface of the second PCBA such that the second flow path is disposed proximate the second sensing element such that at least a portion of the second flowing media makes direct contact with the second sensing element; and wherein rotating the sensor module comprises rotating the sensor module such that at least a first portion of the second flow tube is captured by the first twist-lock arm and at least a second portion of the second flow tube is captured by the second twist-lock arm.

* * * * *